United States Patent [19]

Shrimpton

[11] 4,327,177

[45] Apr. 27, 1982

[54] METHOD AND MEANS FOR CONTROLLING THE SEX OF MAMMALIAN OFFSPRING AND PRODUCT THEREFOR

[76] Inventor: Wallace Shrimpton, 320 Judah St., San Francisco, Calif. 94122

[21] Appl. No.: 179,044

[22] Filed: Aug. 18, 1980

Related U.S. Application Data

[62] Division of Ser. No. 564,807, Apr. 3, 1975, abandoned, which is a division of Ser. No. 814,906, Apr. 10, 1969, Pat. No. 3,894,529.

[51] Int. Cl.³ .............................................. A01N 1/02
[52] U.S. Cl. ...................................................... 435/2
[58] Field of Search ............................................. 435/2

[56] References Cited

U.S. PATENT DOCUMENTS 3,185,623  5/1965  Smith et al. ............................ 435/2

FOREIGN PATENT DOCUMENTS 6604149  9/1966  Netherlands ........................... 435/2

OTHER PUBLICATIONS

J. Reprod. Fert. (1966) 11, 469–472, Schilling.
Bhattacharya, Reprint from "Zeitschrift fur Wissenschaftliche Zoologie", Akademishe Verlagsgesellschaft Geest & Portig, K. G., Leipzig.
Chemical Abstracts, vol. 68, 1963, 66311n.
The Australasian Journal of Pharmacy, Science Supplement, No. 77, Jul. 1969, pp. 549 & 550.

Primary Examiner—Frederick E. Waddell
Attorney, Agent, or Firm—James F. Mitchell

[57] ABSTRACT

A method of controlling the sex of mammalian offspring by separating spermatozoa into fractions having the desired sex characteristics and artificially inseminating the female to produce offspring of the desired sex. The sperm is separated by applying a buoyant force or forces to a mixture of sperm in nutrient media so that separation occurs according to density of the sperm. The nutrient media is controlled as to density characteristics and can have a uniform density gradient from top to bottom so that buoyant forces within such media are selectively applied to sperm of different density to effect separation of the sperm and to hold sperm fractions of different density in suspended relation within the nutrient media. Substantially pure sperm fractions (having the desired male or female sex characteristics) are isolated at the top or at the bottom of a separation column for use in artificially inseminating the female. Under certain circumstances, separation of the sperm into fractions is enhanced by the application of gas pressure (positive or negative) above the mixture of sperm and nutrient media in the column.

13 Claims, 10 Drawing Figures

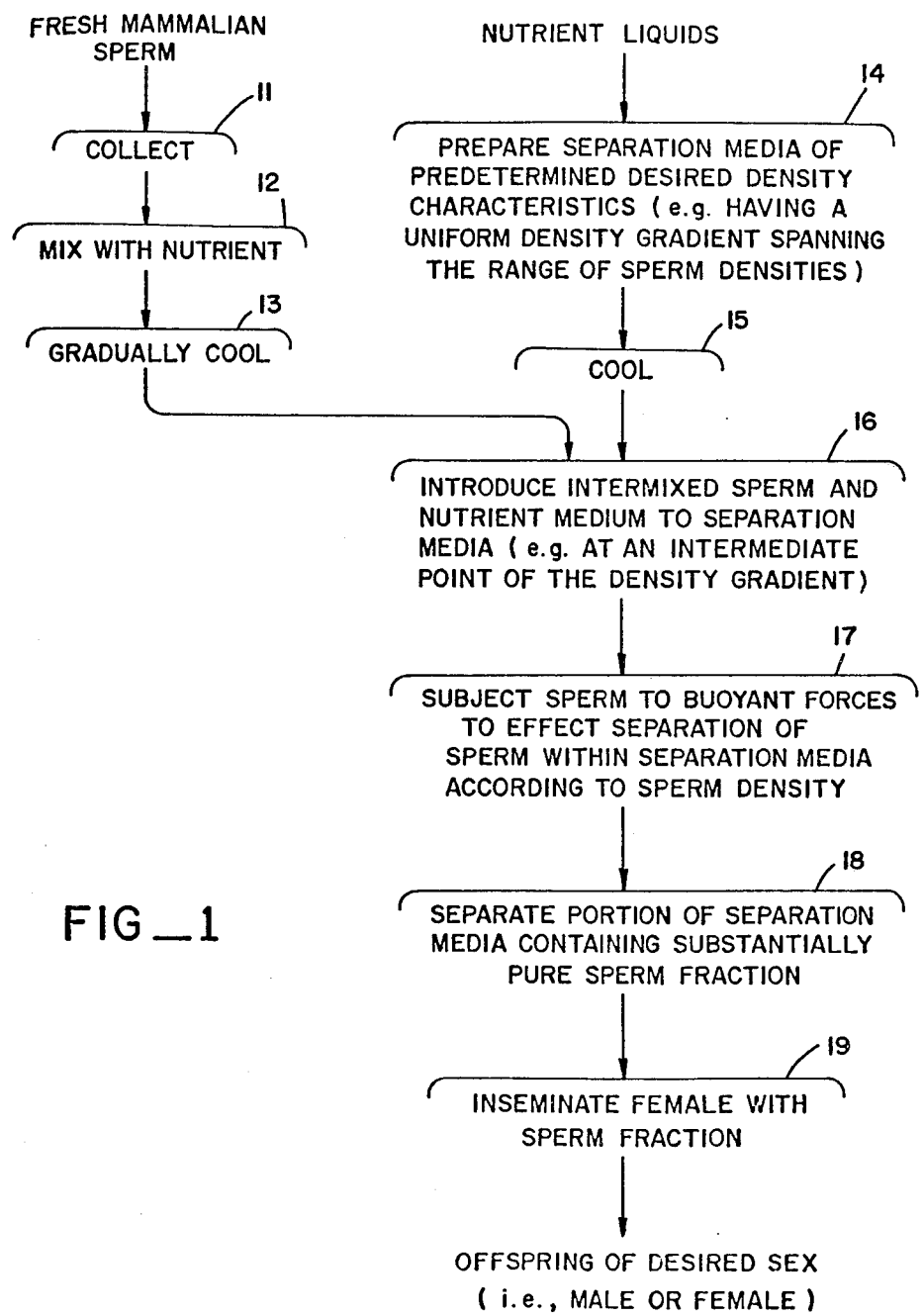
FIG—1

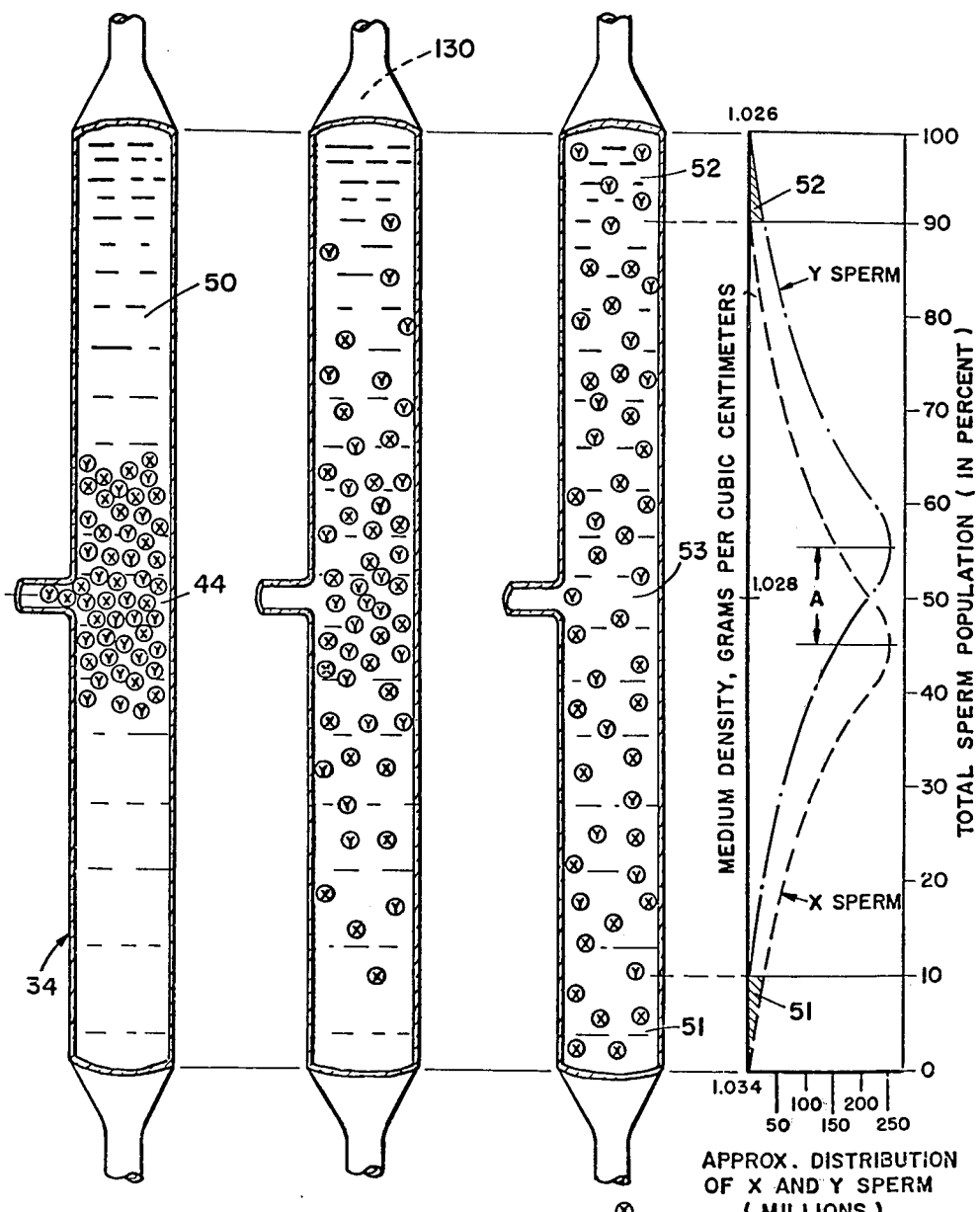

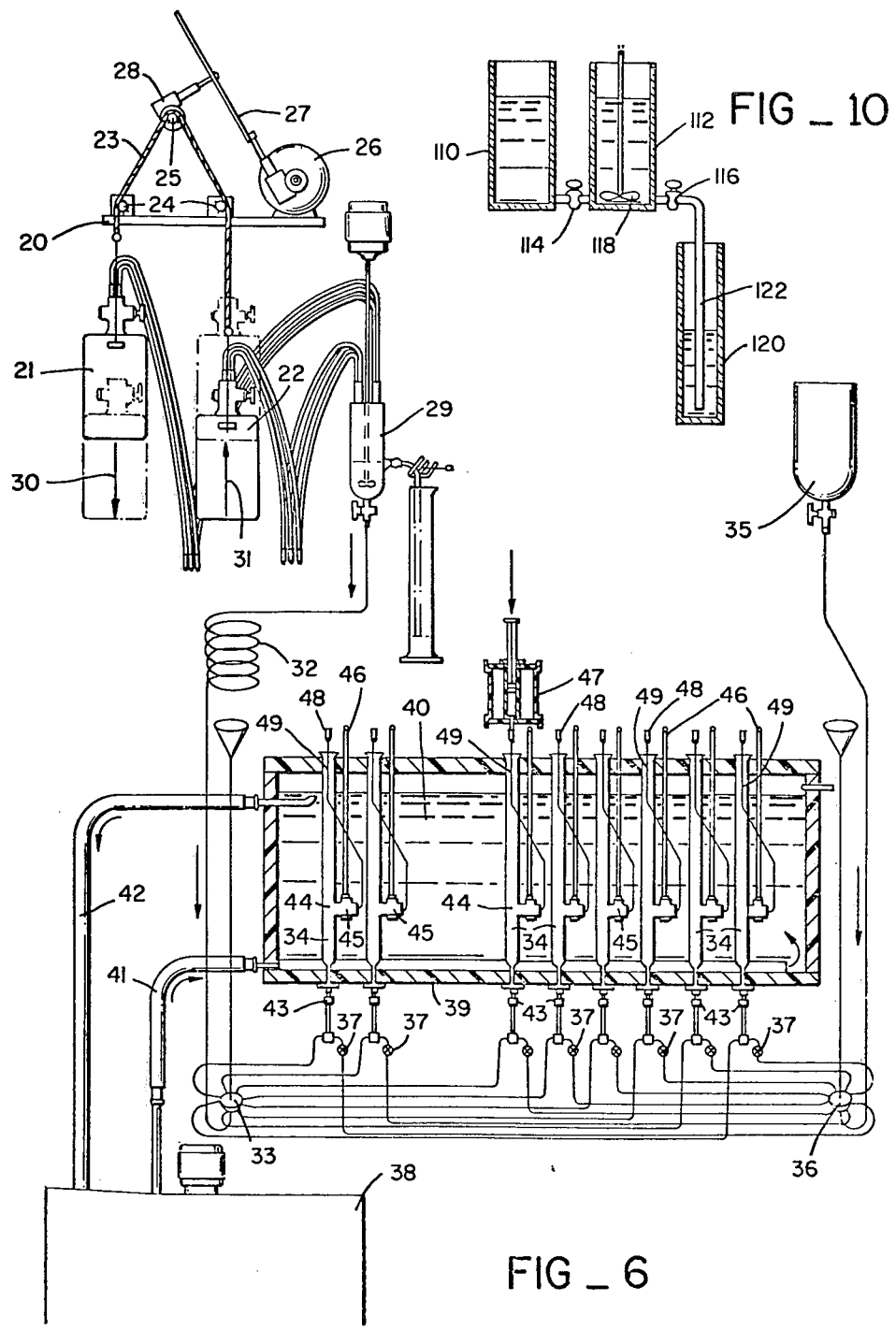

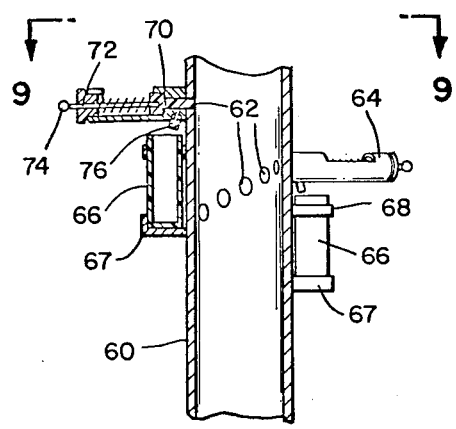
FIG_8
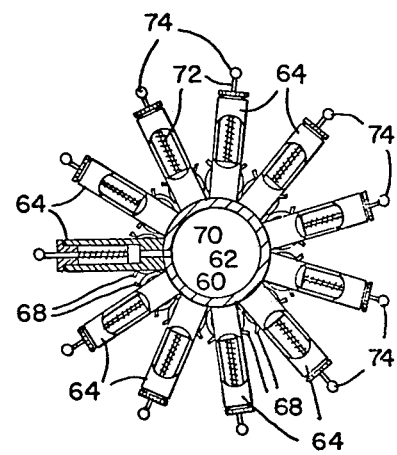
FIG_9
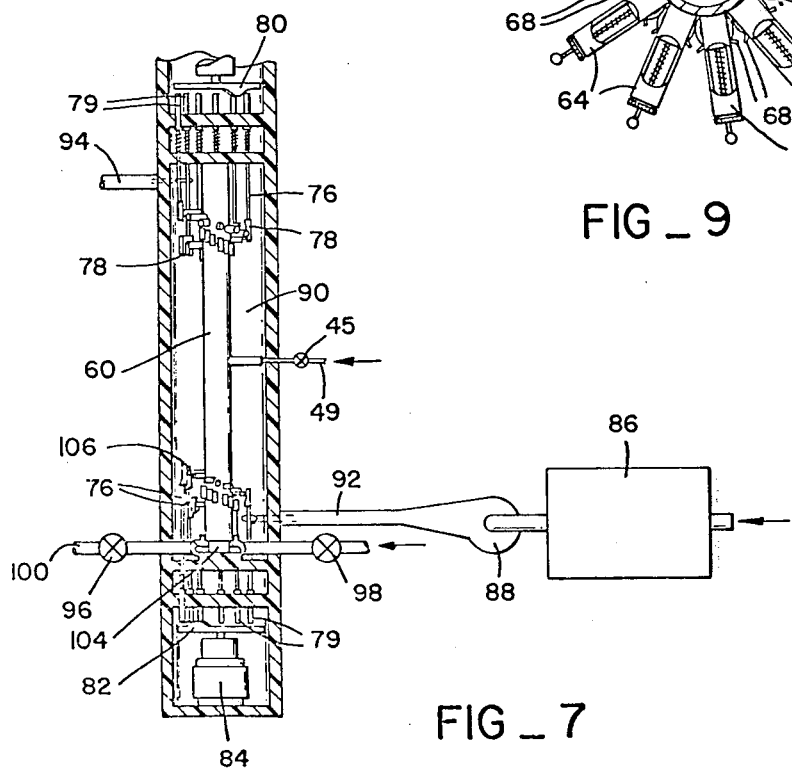
FIG_7

METHOD AND MEANS FOR CONTROLLING THE SEX OF MAMMALIAN OFFSPRING AND PRODUCT THEREFOR

BACKGROUND OF THE INVENTION

It has been determined that the sex of offspring is controlled by the chromosomes of the particular spermotozoon or sperm cell which fertilizes the egg. More specifically, some of the spermatozoa (hereinafter called "sperm") are genotypically known to contain X chromosomes, which carry female producing genes, while the others contain Y chromosomes, which carry male producing genes. In microscopes, the X chromosomes appear larger in size than the Y chromosomes. When a sperm containing X chromosomes (hereinafter called X-sperm) combines with the egg (which contains X chromosomes), female offspring results. When a sperm containing the Y chromosomes (hereinafter call Y-sperm) combines with the egg, male offspring results. The sperm population in an ejaculate of a mammalian male contains both X-sperm and Y-sperm. Heretofore, separation of these sperm in X and Y components has not been satisfactorily achieved. It is evident, however, that a satisfactory procedure for separating the two kinds of sperm, to isolate substantially pure X and Y-sperm fractions, would permit a choice or selection of the ultimate sex of the offspring.

SUMMARY OF THE INVENTION AND OBJECTS

This invention relates generally to a method and means for controlling the sex of mammalian offspring, and to compositions useful in providing offspring of one sex. More particularly the invention relates to a method and means for separating spermatozoa containing X chromosomes from those containing Y chromosomes, to obtain substantially pure fractions of spermatozoa containing either X chromosomes or Y chromosomes.

The present invention is predicated on my discovery that the two sperm genotypes of mammals (X and Y) may be separated according to density characteristics by application of buoyant forces within a liquid separation medium to cause more buoyant sperm to obtain a different level in the separation medium than less buoyant sperm. The term "buoyant force" is used herein to include both positive buoyant forces which cause the sperm to rise or float in the medium and negative buoyant forces which cause the sperm to fall or sediment in the medium. In a preferred practice of the invention, use is made of a separation medium (or media) arranged as a substantially vertical column and having a uniform density gradient from a lightest density at the top to a heaviest density at the bottom. Alternatively, the separation medium is in the form of layers or zones of compatible liquids, each of slightly different density, to similarly provide a separation media which varies from a lightest density at the top to a heaviest density at the bottom of a column. Separation is achieved by introducing a sperm population to the separation medium at a point intermediate the ends of the column, in media equivalent in density to that of the point of introduction, so that the sperm are separated according to density by the simultaneous application of positive and negative buoyancy.

I have found that under carefully controlled conditions a sperm population introduced to a separation column at an intermediate point can be separated, at least in part, by the rise and fall of the sperm related to the individual sperm densities. Moreover, where the separation media has a uniform density gradient, the sperm will achieve a suspended state of separation related to slight density variations in the individual sperm so that desired sperm fractions or layers can be easily separated from the whole. When the range of liquid densities within the density gradient completely encompasses the range or span of individual sperm densities, the sperm fractions or populations at the top and bottom of the column will, when inseminiated, produce offspring of different sex. Finally, the observed phenotypical differences in the sperm obtained from such top and bottom fractions (up to 10% of the total sperm population) have been found to be related to sex genotypes, that is, the top fraction has been found to contain substantially all Y-sperm whereas the bottom fraction has been found to contain substantially all X-sperm.

From the foregoing, it will be apparent that the present invention has utility wherever it is desired to control the sex of mammalian offspring. It is of extreme practical and commercial importance in the field of animal husbandry, for example, in permtting the breeder or farmer to have a choice in selecting the sex of animal offspring.

In general, a principal object of the present invention is to provide a truly successful method for controlling the sex of mammalian offspring.

A further object of the present invention is to provide a method for separating the X-sperm and Y-sperm in the ejaculate of a mammalian male, to obtain substantially pure fractions containing either X-sperm or Y-sperm, useful in artificial insemination of the female to obtain the desired sex.

A further object of the invention is to provide novel composition containing either substantially pure X-sperm or substantially pure Y-sperm, capable of producing mammalian offspring of the desired sex.

A further object of the invention is to provide novel means for carrying out the sperm separation method of the present invention.

A further object of the invention is to provide a novel method and means of the above character which makes possible the separation of substantially pure fractions of X-sperm and Y-sperm, capable of producing normal fertilization.

Additional objects and advantages of the invention will appear from the following description in which the preferred embodiments have been set forth in detail in conjunction with the accompanying drawing.

BRIEF DESCRIPTION OF THE DRAWING

FIG. 1 is a flow sheet illustrating the method of the present invention.

FIGS. 2, 3 and 4 are schematic representations of a particular step in the processing, at various points in time.

FIG. 5 is a graphical representation corresponding in point of time to the schematic representation of FIG. 4.

FIG. 6 is a schematic representation of one system of apparatus useful in carrying out the method of the present invention.

FIG. 7 is a fragmentary view in section and elevation of another embodiment of apparatus useful in carrying out the method of the present invention.

FIG. 8 is an enlarged detail view in section and elevation of a portion of the apparatus shown in FIG. 7.

FIG. 9 is a view horizontal section along the lines 9—9 of FIG. 8.

FIG. 10 is a schematic representation of a further embodiment of apparatus useful in carrying out the invention.

DESCRIPTION OF THE PREFERRED EMBODIMENT

FIG. 1 is a flow sheet illustrating the method of the present invention. In step 11, fresh sperm is collected from the male, containing approximately equal amounts of X-sperm and Y-sperm. This sperm is mixed with a nutrient medium in step 12, following which the mixture of sperm and medium is gradually cooled in step 13. The cooled mixture of sperm and medium is next subjected to processing in steps 16 and 17 to effect separation of the sperm according to density. This latter processing is carried out in the presence of a separation media which has been previously prepared to provide predetermined desired density characteristics, as in step 14. In a preferred practice of the invention, the processing in step 14 provides the separation media with a uniform density gradient sufficient to span the range of individual sperm densities. Following preparation of the separation media, it is cooled to a temperature to immobilize the sperm, in step 15. The intermixed sperm and nutrient medium are also cooled in step 13 to insure substantial immobilization of the sperm, which is then introduced to the separation media in step 16. In the case of a separation media having a uniform density gradient, the sperm is introduced at an intermediate point of the density gradient. Thereafter the sperm is subjected to the buoyant forces within the separation media, in step 17, to cause separation of the sperm according to the individual sperm density. In a density gradient system, the desired sperm fractions achieve a suspended state of separation in the separation media adjacent the top and bottom of the column, thereby facilitating separation of a sperm fraction of desired sex characteristics in step 18. The separated sperm fraction (X-sperm and Y-sperm) can then be employed to inseminate the female, as represented by step 19, to obtain the desired offspring.

The present invention is suitable for use with all mammals. Of particular interest are cattle, swine (i.e., hogs and pigs), human beings and other primates, sheep, rabbits, cats, dogs, goats, horses, donkeys and buffalo. It will be understood that the sperm fraction separated in step 18 is inseminated in step 19 into the female of the species from which the sperm is taken. Of course, horse may be crossed with ass and zebra as may wolf with dog.

The present invention is predicated on determination that there is a difference between the average or mean density of the X-sperm and Y-sperm of mammalian species, the X-sperm being generally more dense that the Y-sperm. For example, in bulls this difference in average density between sperm containing the X- and Y-chromosomes is believed to be about 0.5% at 0° C. In human males and in rabbits, the difference appears to be greater than in bulls.

In general, the medium selected for use in steps 16 and 17 must have a density sufficiently close to that of the sperm so that the slight difference in density between the X- sperm and the Y-sperm will result in the separation of at least part of the sperm into separate fractions containing predominantly X-sperm or Y-sperm. Related to density, viscosity must also be appropriate for controlling the separation. In addition, the medium must not impair the viability or the fertility rate of the sperm, that is, the medium must not harm or destroy the sperm. To the contrary, the medium must provide nutrients to keep the sperm alive. The medium must also have a suitable pH (i.e., within the range from 6.0 to 8.0) to permit it to act as a buffer and to avoid toxic effects or impairment to the fertility of the sperm. The final consideration is that the medium should have the characteristics of a normal body fluid, and, in particular, its osmotic pressure should be within the range from about 277 to 280 millosomos to avoid any possiblity of harmful compression or expansion of the sperm. Throughout the specification and claims, measurement of pH density and viscosity are at 0° C.

I have found that a highly satisfactory nutrient medium for carrying out the separation technique of the present invention is derived from whole mammalian milk and its components. Control of density, for example, in preparing a separation column having a uniform density gradient, can be readily obtained through use of the components of commercially available types of cow's milk. In practice, three media are initially prepared having average densities, respectively, of about 1.025, 1.035 and 1.044. The average density of the lightest media is achieved by using a milk product known as "half-and-half" (meaning that it contains approximately equal portions of homogenized milk and separated cream mixed with ordinary homogenized milk). Thus, an average density of about 1.025 is obtained by mixing half-and-half with small amounts of homogenized milk, as necessary. An intermediate density (e.g., from about 1.034 to about 1.038) is similarly obtained by mixing homogenized milk with small amounts of dialyzed distilled nonfat milk. A relatively dense media of average density 1.044 is prepared by mixing a larger proportion of dialyzed distilled nonfat milk with homogenized milk. Antibiotics to protect the sperm introduced to the medium can also be employed.

Fresh mammalian milk such as cow's milk and its components have a suitable viscosity, density and pH (about 6.4 to 6.8) for use in carrying out my separation process. Cow's milk is also a normal body fluid, making it appropriate for use generally as a medium. Since mammalian milk is approximately isotonic with the blood of the animal from which it is drawn, its osmotic pressure or osmolarity is also more easily adjusted to a value compatible with that of the sperm (i.e., between about 276 and 300 miliosmos). As hereinafter described (see specific examples), specific desired values of density, viscosity, osmolality, and pH can easily be obtained during the operations to prepare the separation media for use in the sperm separation steps.

Satisfactory nutrient liquids are also derived from other mammalian sources (e.g., human milk) or derivatives of mammalian milk (e.g., milk powder). Nutrient liquids based on egg yolk, dextrose, coconut cream (derived from green coconuts), tomato juice, glucose, fructose, lecithin, amino acids, living body fluids and extracts, tissure extracts (e.g., liver extract), and mixtures of these, are also satisfactory. Egg yolk particularly includes glucose, fructose, and amino acids which provide nutriments and assist in fertility. When used in conjunction with glycine, desired values for density, viscosity, osmolality and pH can be obtained. The glycine (preferably and aqueous solution of 2 to 5% glycine) serves to buffer the pH and to depress the freezing point of the egg yolk in the medium. In general, the ratio of glycine to egg yolk depends principally upon the initial density, viscosity, and osmolality of the egg yolk. The ratio can be varied, of course, as may be necessary in preparing a uniform density gradient. Since the glycine solution has a lower viscosity than the egg yolk, more will be required where a viscosity depressant is also needed. Generally, bases on a 4% glycine solution, one part of glycine will be required for each one to four parts of egg yolk, depending on density requirements.

As previously noted, the separation method of the present invention is best carried out in conjunction with a separation media having a uniform density gradient. While various procedures are known for the preparation of density gradient columns, one particularly satisfactory procedure is carried out in connection with apparatus as generally represented at 20 in FIG. 6. Thus, assuming the use of three separate media based on cow's milk, each adjusted to an average desired density in the manner previously described, the medium of lightest average density (e.g., 1.025) is placed in the uppermost container 21. The media with an intermediate average density (e.g., 1.035) is placed in the lower container 22. As illustrated, the two containers, 21, 22 are suspended on a pulley arrangement which functions to raise the container 22 at the same rate that it lowers the container 21. More specifically, the separate containers are suspended from the ends of a chain 23 reeved about the rotary supports 24 and the drive pulley 25. The entire unit is powered by the motor 26 through the drive take-off 27 and worm gear arrangement 28. As will be understood, the illustrated apparatus serves to simultaneously introduce the liquids from the containers 21 and 22 to a mixing chamber 29, at controller rates of flow determined by the hydrostatic or liquid head for the media in each container as respects the mixing chamber. Thus, the flow of the less dense nutrient media in container 21 begins at a maximum and decreases to a minimum, as represented by the dotted line 30. In like fashion the flow of the denser nutrient medium in container 22 begins at a minimum and increases to a maximum, as represented by the dotted line 31. On the other hand, the total flow at any time through the mixing chamber 29 remains constant. The mixture discharged from the bottom of the mixing chamber 29 will therefore have a linear density gradient ranging from the density of the lightest media in container 21 to that of the intermediate media in container 22. A desired intermixing of the media introduced to the mixing chamber 29 is accomplished by conventional agitation means, for example, as illustrated in FIG. 6.

In the use of the apparatus shown in FIG. 6, a media having the desribed linear density gradient passes from the mixing chamber 29 through a surge coil 32 to a vented manifold 33, whence it is discharged in equal proportionate amounts to the bottom of the various separation columns, represented at 34. To facilitate use of the apparatus, a medium of relatively heavier average density (e.g., 1.044) is placed in a third container 35 from which it can be introduced to the bottoms of the columns 34 through the separate vented manifold 36, under control of the valving means 37. As hereinafter explained, the heavier medium in container 35 is used to adjust the height of the density gradient columns within the separation devices 34.

In carrying out the separation method of the invention, the separation media is introduced to form substantially uniform density gradient columns within each of the separation devices 34 and thereafter is gradually cooled to a temperature which will immobilze without harming the sperm. In the illustrated apparatus, this cooling is accomplished by a circulatory refrigeration apparatus including the refrigeration unit 38, the cooling tank 39 surrounding the separations devices, and a body of cooling water 40 containing glycerol which is circulated between the refrigeration unit and a tank by the inlet and outlet conduits 41 and 42, respectively. With conventional cooling equipment, cooling of the density gradient columns within the separation devices from room temperatures to a temperature below about 1° C. is accomplished in a very short period of time, ranging from a few minutes up to a few hours, at the most.

Prior to initiating the separation, fresh sperm is collected and intermixed with a nutrient medium of the same type and corresponding in density to an average of median density of the media forming the density gradient column (e.g., about 1.028 in the system described). The sperm sample is also pre-cooled to a temperature below 1° C. and thereafter, as illustrated in FIGS. 2 and 6, is introduced to the separation column at an intermediate point of the density gradient column. For best results, the density of the sperm plus extender sample should correspond closely to the density of the separation media at the point of introduction. To insure that this occurs, a small amount of the nutrient medium for the sperm can be initially introduced to the separation column, preferably containing small amount of coloring ingredient so its relative density with respect to that of the column can be readily determined by the movement of the colored segment within the column. Thus if the position of the colored insert indicates that the density gradient column in a particular device 34 should be adjusted upward, a small amount of the heavier medium in the container 35 can be introduced through the manifold 36 and valving means 37 to the bottom of the density gradient column in question. On the other hand, if a particular density gradient column is too high within its separation device 34, a small amount of the separation media originally present can be discharged through the stopcocks 43 positioned at the bottom of each of the separation columns 34. The important consideration is that the density of the separation medium opposite the point of sperm introduction (represented at 44 in FIGS. 2 and 5) be approximately equal to that of the nutrient medium containing the introduced sperm.

With reference to FIG. 6, each of the separation columns 34 is provided with inlet valving means 45 operable by the valve controls 46. At such time as the sperm is to be introduced to the separation columns, the sperm within refrigerated containers 47 is moved to positions adjacent the filling spouts 48. The valve controls 46 are then operated to introduce the sperm through the filling lines 49 to the midpoints of the density gradient columns contained within the separation devices 34.

Within the density gradient columns, represented at 50 in FIGS. 2 to 4, positive and negative buoyant forces are applied to the sperm to cause the less dense sperm to rise into upper portions of the column and the more dense sperm to sediment into lower portions of the column. Thus as particularly illustrated in FIG. 2, the less dense sperm move at a relatively rapid rate into the upper portions of the column due to substantial relative density differences existing at the point of introduction. As the lighter sperm rise in the column they encounter separation media of gradually decreasing density within the density gradient (FIG. 3), with the result that the individual sperm eventually achieve a state of suspension within the separation medium related to its own density. In similar fashion, the more dense sperm rapidly sediment into the bottom portions of the column, gradually losing sedimentation velocity until such time as they likewise achieve a state of suspension in the lower portions of the separation column.

While it has been determined that the X-sperm are generally heavier than the Y-sperm, this is not uniformly so. Instead, I have found that there is a normal Gaussian distribution of the two populations so that the difference in density between the X and Y sperm, as previously indicated, represents a difference between the mean or average densities of the two populations. Thus, referring to FIG. 5, which is a plot of the distribution of the different populations with reference to varying density within the columns, this difference in mean density is represented by the dimension A. On the other hand, as represented in both FIGS. 4 and 5, the separation by density of the X and Y populations according to relative density makes possible the isolation of substantially pure X and Y sperm populations at the top and bottom of the separation columns. These isolated substantially pure fractions are represented by the sperm populations shown in zones 51 and 52. As a practical matter, I have found that the sperm capable of being isolated in either of these zones generally comprise less than 10% of the total sperm population. On the other hand, since the ejaculate of a mammalian male normally contains many millions of sperm (e.g., a portion of the ejaculate will average 400 million sperm for a typical male bull), the number of sperm present in one or more of the isolated fractions (i.e., 20 to 60 million sperm) is sufficiently large under normal circumstances to permit insemination and conception of offspring of the desired sex. Moreover, the intermixed sperm contained within the intermediate portion of the column, represented at 53 in FIG. 4, is not lost, but remains available for use by animal breeders and the like to effect normal artificial insemination wherever sex predetermination or control is not desired.

It will be understood that the separate indications in FIGS. 2 to 4 represent different points in time. Thus, FIG. 2 illustrates the point of introducing the sperm to the columns. FIG. 3 represents a point in time where the sperm are still in motion, due to the continuing effect of the buoyant forces within the separation media (positive and negative) upon the individual sperm. FIG. 4 represents a final equilibrium condition wherein the individual sperm have achieved a state of suspension within the density gradient of the separation medium, according to individual densities. With any particular separation media satisfactory for use in my process, I have found that the time required to reach the equilibrium state may vary only slightly from one separation to the next. On the other hand, slight differences in temperature or in the viscosity of the separation media may cause the time necessary to completely carry out the separation process to vary considerably. Generally, no more than 24 hours are needed in any event, to carry the separation process to the equilibrium state. In fact, about ½ to 4 hours is usually sufficient, with about 2½ hours being indicated as optimum.

It will be evident that if insufficient time is used for separation, the equilibrium state may not be achieved and the separation of pure sperm fractions may not result. On the other hand, if more than about 24 hours are taken in the separation step, the medium itself may tend to separate. That is, the inorganic ions and other heavy particles in the colloid medium may separate after long periods of time. Moreover, the particles of the medium may tend to "salt out" or precipitate from the fluid if substantially more than 24 hours are used.

For best results, assuming the use of a density gradient column, the median density of the separation medium (i.e., at the midpoint) should be close to the median density of the sperm of the mammal from which the sperm is taken. With respect to humans and bulls, the density range is about 1.01 to about 1.19 grams per cubic centimeter, with the median density falling in the range from about 1.028 to about 1.036. In practice, I have found that a density gradient column for use in separating bull and human sperm should range from about 1.010 to about 1.150 grams per cubic centimeter, with a median density of the order of 1.028. If the median density of the density gradient column approaches the upper limits of the density range, the lighter X-sperm will tend to commingle with the Y-sperm at the upper end of the column so that separation of a pure Y-sperm fraction becomes difficult if not impossible. In like fashion, if the median density of the density gradient column falls too close to the lower limits of the density range, the heavier Y-sperm will tend to commingle with the X-sperm so that separation of pure X-sperm fraction is impaired. Consequently, in order to insure a separation of substantially pure fractions of X-sperm and Y-sperm, the median density of the density gradient column should closely approximate the average density of the sperm sample. In addition, the range of densities in the density gradient column should be sufficient to insure that a full range of rise and fall of the sperm is permitted, particularly as respects the lightest Y-sperm and the heaviest X-sperm at the extreme density ranges of the sperm sample.

The viscosity of the separation medium should also fall within a predetermined viscosity range for satisfactory separation. In general, the viscosity of the separation medium is related to the density. For humans, rabbits and cattle, viscosity should be between 2 to 9 centipoise measured at 0° C.

Table 1 sets forth the range of densities and viscosities for various species of mammals, and also indicates a median density and viscosity of satisfactory separation in a density gradient column. All measurements taken in Table 1 are at 0° C., with the density in grams per cc and viscosity in centipoise.

TABLE 1

| | Density | | | |
| --- | --- | --- | --- | --- |
| | Low | High | Median | Viscosity at 0°C. |
| Human | 1.015 | 1.09 | 1.017–1.030 | 2–9 Centipoise |
| Rabbit | 1.015 | 1.09 | 1.022–1.030 | 2–9 Centipoise |
| Bull | 1.020 | 1.10 | 1.027–1.032 | 2–9 Centipoise |

While the osmotic pressure of the medium may vary between a lower limit of about 276 and an upper limit of about 300 milliosmois, as a practical matter I have found that best results are obtained when the osmotic pressure of the medium is about 280 milliosmois.

Depending on the medium employed, a temperature between about −5° C. and about 2° C. is required. Below this temperature range, the physical properties of the medium are changed to such an extent that the desired rise and fall of the sperm to achieve a desired state of suspended separation will not result. At higher temperatures, the sperm tend to swim or move on their own through the medium so that the buoyant forces within the separation medium fail to separate the sperm as substantially inert particles. Accordingly, a preferred temperature for use of a density gradient column prepared from whole mammalian milk is 0.8° C.

During the process care must be taken to avoid excessive vibration. Violent shaking tends to tear the trails from the sperm. Moreover, during the separation sequence, steps 16 and 17, even slight vibrations will affect the rise and fall of the individual sperm so that they do not act as inert particles. In the steps of separating the sperm fractions, step 19, particular care is required to avoid vibration and resultant intermixing and contamination of adjacent fractions.

Another factor to be considered is the avoidance of visible light. Light affects the fertility of the sperm. Fertility can also be affected by extremely high or lower pH of the medium (outside the range 6.0 to 6.8 for most species), age of the sperm, and number of mobile sperm.

The use of a density gradient column results in a suspended state of separation of the sperm according to sperm density. Once the sperm have achieved the equlibrium state, represented in FIG. 4, the desired substantially pure sperm fractions should be immediately separated from the top or bottom of the column and preserved for artificial insemination. With the aparatus of FIG. 6, it is a relatively simple matter to withdraw the X-sperm fractions from the bottom of the columns 34 through the stopcocks 43. However, to avoid intermixing of adjacent fractions, it is desirable to drain drop-by-drop with about 5 to 10 seconds per drop. It will be understood that the Y-sperm fraction at the top of the column is done by draining the entire column, with the Y-sperm fraction being the last to be recovered. Alternatively, the Y-sperm fraction may be initially removed from the top of the column with a special apparatus for this purpose, for example, a special burette fitted with a Pasteur pipette.

Referring to FIG. 7, apparatus is shown which is particularly useful in initially removing the uppermost or Y-sperm fraction from the top of the column. As particularly shown in FIGS. 8 and 9, the separation apparatus comprises a cylindrical burette or column 60, suitably provided with apertures 62 along its length to facilitate the separation of closely spaced liquid fractions. Each of the apertures 62 is in communication with a separating or fractionating valve mechanism 64 which controls the discharge of a sperm fraction into the receiving vials 66 mounted on the column by means of the bottom supports 67 and clips 68. Thus, as best seen in FIG. 8, each aperture 62 is closed by a spring biased valve member 70 operable by a pull rod 72. The pull rod can be actuated through the pulls 74 to move outwardly, thereby discharging a sperm fraction through the discharge spout 76 into the vial 66. Since individual valving mechanisms 64 and vials 66 are spaced along the length of the column with respect to each aperture 62, the illustrated mechanism makes possible the separation of minute fractions along the entire length of the column. Alternatively, of course, a larger specimen may be withdrawn from a substantially larger portion of the column by operation of a single valving mechanism 64 at the bottom of a desired column length. The vials 66 can thus be made sufficiently large to accommodate the volume of the several fractions, as may be necessary.

As illustrated in FIG. 7, the individual valving mechanisms 64 are constructed to be operated in automatic or semi-automatic fashion by means of the cam actuated rod and actuator mechanisms 76, 78. The latter are adapted to engage between the actuators 74 of the pull rods and the body of the valve mechanisms 64, to bias the valve members 70 outwardly. Thus as particularly illustrated in FIG. 7, each of the valve actuators 76 and 78 are provided with spring biased cam followers 79 which cooperate with the rotating cams 80 and 82 at the top and bottom of the column respectively. The cam actuators can be rotated at a predetermined rate to effect a desired sequential operation of the valving mechanism 64 by suitable drive means (e.g., a variable speed electric motor) at the bottom of the column and similar means at the top (not shown). It will be understood that the number of positioning of the valve actuators 78 with respect to the camming mechanisms can be predetermined to facilitate fractional separation of sperm samples from the interior of the column 60, as may be appropriate to a particular separation technique.

FIG. 7 illustrates the mounting of the separating column 60 within a refrigeration enclosure. In view of the use of sperm collecting vials 66, cooling of the columns in this embodiment is accomplished through the use of a dry gaseous atmosphere, for example, dry cold air at a temperature below about 1° C. Refrigerated gas for the cooling operation may be supplied by any appropriate means, as represented by the refrigeration chamber 86 and impeller 88, which supply refrigerated gas to the cooling chamber 90 through the conduit 92. Cooling gas discharged from the outlet 94 may be recovered for recycling or discharged to the atmosphere, depending upon the particular cooling system employed. In other respects the separating column 60 is employed in the separation process in similar fashion to the processing described with respect to columns 34, valving mechanisms 96 and 98 being the counterparts of the manifolds 33 and 36 in the apparatus of FIG. 6. As illustrated, the valving mechanisms 96, 98 and the associated conduits 100, 102 are in direct communication with the bottom opening of the columns 60 (i.e., through chamber 104).

In a typical use of the apparatus illustrated in FIGS. 7 to 9, the columns 60 are prepared in the previous manner by introducing a separation media of predetermined desired density characteristics. Each column is then cooled by suitable application of the refrigeration unit and circulating system 86, 88 to obtain a desired temperature of the separation media. The sperm samples to be separated are likewise prepared by intermixing with a nutrient medium in the manner previously described. Assuming the use of density gradient columns, the vertical position of the separation media or columns can be adjusted by the technique previously described. A sperm sample, after being first gradually cooled to immobilize the sperm, is then injected through the conduit 49 and valving mechanism 45 at the point of average or median density to initiate the sperm separation through action of the buoyant forces within the density gradient column. After equilibrium conditions have been reached, the camming mechanisms for the valve operators 78 are energized to initiate withdrawal of sperm fractions. In a preferred technique, the sperm fractions are withdrawn from the top of the column in descending fashion, to obtain susbstantially pure fractions of the lightest sperm (Y-sperm). The central portion of the column 60 is then discharged in a single operation through a timed operation of a particular valving mechanism (e.g., 106 in FIG. 7) obtained by a timed deactivation of the cam motor 84. When the central portion of the column has been drained, the cam motor 84 is energized to draw off the lowermost fractions, again descending from the top, to obtain the heaviest sperm fractions (X-sperm). In other words, the actuation of the cams in the upper portion of the column serve to draw off the sperm fraction in the zone 52 (see FIG. 4), whereas the actuation of the valve mechanisms adjacent the bottom of the column serve to separate the sperm fraction in zone 51.

Under certain conditions, the separation processing is facilitated by use of a gas under positive pressure (i.e., 0.1 to 10 psi) in the head space above the separation media in the column 60. Such gaseous pressure which may be exerted by a cold dry air or an inert gas such as $N_2$ or $CO_2$, supplements the hydrostatic head serving to discharge the sperm fractions into the vials 66. Such use of gas under pressure is particularly useful, for example, in facilitating discharge of the intermediate sperm fractions through the valving mechanism 106.

In preparing the separation media in the form of density gradient column for use in operations just described, various techniques can be employed in addition to those shown and described with reference to the apparatus in FIG. 5. For example, a milk media can be appropriately prepared to a desired density gradient by subjecting commerically available homogenized milk to the substantial centrifugal forces possible with modern ultracentrifuges. Such devices, which rotate at speeds in excess of 1000 revolutions per minute, generate forces enormously greater than gravity. The result of such centrifugation is to distribute the molecules in solution in the centrifuge cell in such a way that the density is higher the greater the distance from the center of the rotor. I have found that a milk media with a desired density gradient can be prepared in relatively short time with ordinary laboratory centrifuges, without any change in the osmolality of the milk media which remains substantially constant throughout the density gradient. The range of the density gradient can also be varied by using mixtures of half-and-half and homogenized milk to vary the starting fat content. Control over the density gradient can additionally be obtained by variations in the speed and time of centrifugation.

To facilitate practice of the invention in relatively underdeveloped countries, even simpler procedures are available for preparation of density gradients. One such procedure is illustrated in FIG. 10 which illustrates interconnected vessels 110 and 112 which may be simultaneously discharged by valve means 114 and 116. In this procedure, the dense liquid contained in vessel 110 is introduced into the bottom of the vessel 112 containing the less dense liquid, where the two liquids are mixed by a simple propeller agitator 118. The resulting mixture flows out of the vessel 112 through a tube 122 that leads to the bottom of the density gradient column being formed in the column 120. If the rate at which the denser liquid flows from the vessel 110 is exactly half the rate at which the mixture flows out of the vessel 112, a linear density gradient will be formed in the column 120, with the denser liquid at the bottom and the less dense liquid at the top. An even simpler way to produce a density gradient is to pour a lighter liquid gently over a heavier liquid, initially poured into the bottom of the column. With time, interdiffusion of the two miscible liquids will nullify the transition zone between the liquids of different density to eventually achieve a linear gradient, varying more or less directly with the height of the column. This technique can be speeded by the use of very gentle agitation at the transition point between the liquids of different density.

The processing of the present invention makes possible the separation of sperm fractions of varying degrees of purity, that is, fractions containing varying amounts of either X-sperm and Y-sperm. As represented in FIG. 4, which is typical of conditions actually achieved with the sperm of the mammalian species herein mentioned, the separation of substantially pure fractions of X-sperm or Y-sperm is possible, and has been obtained by the present method (see specific examples). Thus, as previously mentioned, the zone 52 in FIG. 4 contains substantially pure Y-sperm. The fraction contained in zone 51 contains substantially pure X-sperm. Fractions effective to carry out the purposes of the present invention should have at least 70 to 80% of either the X-sperm or the Y-sperm (according to the selection) to overcome the 50—50 ratio existing in nature. For commercial purposes, at least 70 to 80% of either the sperm should be of the desired sex, if the expense involved in carrying out the method is not to be prohibitive. While a fraction containing at least 90% of sperm of a single type is essential to reduce the chance of obtaining offspring of the opposite sex to a statistically tolerable rate, a fraction substantially 100% pure would, of course, be the most desirable since there would be no chance of error. The complete separation of a pure fraction, made possible by the present invention, assures that if there is any conception at all, the offspring will be of the desired sex. Thus, where separation of a substantially pure fraction is accomplished, as in FIG. 4, each of the fractions represented by the sperm in zones 51 and 52 comprises essentially sperm having only the desired chromosomes in a carrier.

In carrying out the separation procedures herein described, it is desirable to have a procedure for testing the various fractions to determine the density of the solution. I have found that one suitable procedure involves means for measuring density, such as a plurality of containers containing solutions of known varying density (e.g., $CuSo_4$) into which droplets of media may be introduced to determine density. As an alternative embodiment, a plurality of small hydrometers might be placed in the separation column to determine different density levels within the column, this latter embodiment would avoid the necessity of taking small fractions and testing each one.

When mammalian milk or body fluid is used as a separation medium, determination of the density in various zones within the separation column may be determined without draining by using monochromatic light or radiant energy of various frequencies that measure the opacity of the mixture. Thus, with a transparent or translucent mixture, such as milk, a light source may be placed on one side of the column and a photoelectric cell on the other side (connected to an amplifier and a recorder) to measure the opacity of the mixture to determine where the separated layers of sperm are located.

Location of desired density layers or the desired fractionating point between the desired density layers, may also be determined by measuring the conductivity at various points in the column. Thus, multiple electrodes are placed in the column to determine the change in conductivity of the contents of the column at various points along its length. The conductivity of the separated sperm fractions is different from that of the supporting medium.

Other means for determining the location of the separated sperm fractions include a micro-densitometer, which measures density using poolarized light, and microscope techniques which measure the scattering of polarized light.

In a further embodiment, a gelatin tube may replace the burette forming the separation column. When the separation process has been carried to the state of equilibrium represented by FIG. 4, the tube and its contents are gradually cooled to a temperature well below freezing, for example −20° C., and the separated sperm fractions frozen in situ. The frozen tube may then be cut into appropriate fractions as desired. Storage of the separated sperm fractions for relatively long periods is then possible.

In those cases where the average or mean density between the X-sperm and Y-sperm of the species being separated is quite small, for example, in the case of bulls, the degree or range of effectivenss of the positive and negative buoyant forces within the density gradient column becomes somewhat more critical. I have found that this difficulty can be largely overcome through application of negative gas pressure above the surface of the separation column, to achieve a Cartesian effect. Specifically, I have found that by application of a vacuum in the head space above the separation column (e.g., in the space 130 in FIG. 3), the apparent density of the sperm being separated within the density gradient column is decreased with the apparent density of the Y-sperm at the top end of the tube decreasing to a greater degree than the apparent density of X-sperm at the bottom end of the tube. While the physiological factors underlying this decrease in apparent density is not clearly understood, it is postulated that the spermatozoa have an elastic exterior which is therefore responsive to the negative pressure in the space above the column. By way of illustration, the individual spermatozoa may be compared in the initial state to tiny balloons carrying tiny weights so that the resultant effect of the buoyant forces on the sperm is close to zero (i.e., neither positive nor negative). In such condition, the sperm will tend to move up and down in the media in response to any change in the gas pressure above the media surface. The explanation for this phenomenon is that the separation media is relatively incompressible and readily transmits to the compressible sperm the force of the changing gas pressure, thus causing variations in the volume of the sperm and consequently is apparent density. Consequently, in circumstances where the positive buoyancy is less than desired, so that the Y-sperm do not rise as rapidly as desired in the upper portion of the density gradient column, imposing a negative pressure above the column serves to increase the positive buoyancy and thereby the separation effects of the separation media upon the Y-sperm. In practice, we have found that separation efficiencies can be increased as much as 30 to 50% by application of a vacuum of about 10 to 20 inches of mercury in the head space above the density gradient column. The normal procedure is to apply the vacuum gradually, for example, reaching a vacuum equivalent to 15 inches of mercury in a period of about five minutes. Best results are obtained when the vacuum pump is energized shortly after introduction of the sperm sample to the separation column, with the vacuum being drawing continuously until the end of the separation process. To protect the separated sperm, the vacuum is reduced to zero over a period of at least two minutes, prior to separation of the desired sperm fractions.

As a generalized example, illustrating the practice of the invention, a separation media in the form of a density gradient column can be prepared from commercially available cow's milk and its components by initially heating to 90° F., cooling to room temperature (e.g., 72° F.), filtering all the starting materials (i.e., homogenized commercial milk, half-and-half, distilled nonfat and low-fat milk) through sterilized glass wool at approximately room temperature. After cooling, each component can be treated with suitable antibiotics (e.g., potassium, penicillin g, and streptomycin sulfate solution). In the case of nonfat milk, the value of the density can be increased without substantial change or alteration in the osmotic pressure by dialysis to remove various organic and inorganic salts and without reduction in protein content or other impairment of the milk. The milk is redistilled with vacuum to remove the excess water, thereby achieving the higher density. I have found, for example, that dialysis in laboratory dialysis equipment (e.g., Oxford Multiple Dialyser) for periods of 10 to 15 hours followed by redistillation at 58° C. for about 3 to 10 hours will produce the desired effect. Using the described procedure, the following are representative of typical densities and osmotic pressures obtained with the indicated starting materials, after preparation.

| Media | Osmolality | Density |
| --- | --- | --- |
| Half-and-half | 280 | 1.024 |
| Homogenized milk | 280 | 1.034 |
| Low-fat milk | 348 | 1.043 |
| Distilled nonfat milk | 214 | 1.049 |

Mixtures of the foregoing materials are used to obtain desired densities and osmolalities. Thus, low-fat milk is mixed with distilled nonfat milk to obtain a mixture having an osmolality of approximately 280 and a density substantially above the desired maximum density of 1.044 grams per centimeter. In like fashion, half-and-half is mixed with homogenized milk to obtain a mixture with a compatible osmolality and a desired density of 1.028 grams per centimeter. These mixtures are now mixed to provide a medium of desired maximum density of 1.044 grams per centimeter. Following this procedure media of desired density at 0° C. are readily obtained for use in forming a density gradient in accordance with the procedures herein described, for example with reference to FIG. 6.

To prepare sperm for separation, freshly collected sperm are mixed with a mixture of homogenized milk and half-and-half of known density (e.g., 1.0295) in proportions to provide a population of about 200 to 300 million sperm per cc of media, the total sample providing at least 400 to 600 million sperm for the separation processing. The intermixed sperm and nutrient media are then placed in a cold room and gradually cooled to a temperature close to 0° C. (i.e., 0.8° C.).

The sperm sample is introduced to the "midpoint" of the density gradient column by first determining the location within the column of the zone of average or median density corresponding to that of the sperm sample undergoing separation (e.g., 1.028). This point is easily located by injecting a small amount of color into a separate portion of the medium of density, say, 1.028, and introducing this small amount of colored medium through the inlet valve 45 to a central portion of the column. Thereafter the 1.028 density strata (as determined by the color) is vertically adjusted within the column to a point opposite the inlet valve 45 (FIG. 6).

Prior to initiating separation, the density gradient column is cooled to the desired separation temperature (0.8° C.) and the sperm sample introduced through the filling spout 48 and tube 49 to the midpoint of the density gradient column. Separation of the sperm according to density thereafter occurs through the buoyant effects of the density gradient medium, causing the less dense sperm to rise and the more dense sperm to fall within the density gradient column. After a sufficient period of time to achieve equilibrium (e.g, about 2½ hours), a sperm fraction is separated from the top or bottom of the column (according to selection) to obtain nutrient media containing a sperm fraction comprising from 4 to 8% of the total sperm population in the sample introduced. In the case of X-sperm, the sperm fraction is separated from the bottom of the column in any of the manners previously described. Where Y-sperm are desired, the sperm fraction is similarly separated from the top of the column. In practice, the separated fraction is counted for the number of sperm present therein, and the number plotted against the fraction.

The practice of the invention is exemplified in the following generalized procedure which was used in a number of separations (in excess of fifty) to obtain the results hereinafter tabulated. In carrying out the separation specified, using apparatus as in FIG. 6, a series of density gradient columns were simultaneously prepared in each of the columns 44. The density gradient in each column ranged from 1.0255 at the top to 1.044 at the bottom (accomplished by use of a medium of density to 1.0255 in container 21 and 1.036 in container 22). Sufficient time was then allowed to permit the density gradient columns to cool to the temperature of the water bath 40 in the refrigeration tank 39 (0.8° C.), thirty minutes being sufficient for such purpose. The column height was adjusted to show a density of 1.0295 at the inlet point opposite the valve mechanism 45.

Prior to initiating separation, fresh bull sperm was collected and intermixed with a nutrient medium having a density of approximately 1.0295, following which the density of the intermixed sperm and nutrient medium was adjusted to a final density of 1.0295, adding higher density or lower density medium as necessary. The sperm and nutrient medium were then cooled for approximately two hours to gradually cool the sperm to an immobilization temperature of 1° C. (i.e., 0.8° C.). Sperm samples containing approximately 480 million sperm (e.g., 1 to 2½ cc of intermixed sperm and nutrient medium) were introduced to the individual separation columns through the side tubes 49 and valve mechanisms 45, using a hypodermic syringe 47 cooled to a sperm immobilizing temperature of 0.8° C. Sperm was introduced to the column at a relatively slow rate, not exceeding about 1 cc per minute. To insure that all the sperm were introduced to the columns, a small amount of nutrient medium was additionally pushed through the side tubes 49 thereby clearing the side tubes of sperm. Following the introduction of the sperm, which was done under infra-red light conditions, the refrigeration tank and separation columns were covered to exclude light during the separation processing. Separation of the sperm occurred through operation of the buoyant forces within the density gradient columns over a period of 1 to 4 hours (optimum 2½ hours) and thereafter under subdued light, sperm fractions were removed from the top of the columns by means of pipettes equipped with water pumps (hereinbefore described) following which the more dense sperm fraction was removed from the bottoms of the column, (as represented at 34), through the stopcocks 43 at the bottom of the columns. To insure purity of the separated fractions, the portions removed from the top and bottom of density gradient columns were maintained at a volume of approximately ¼ cc.

Intermixed sperm fractions were also removed from central portions of the column. All of the sperm samples were then checked for sperm count, using a standard procedure with a haemacytometer.

The separated fractions of relatively pure sperm (¼ cc) were subsequently mixed with a small quantity (0.165 cc) of 15% glycerol in homogenized milk, and the mixture held 15 minutes at 1° to 8° C. After a holding period of approximately 15 minutes, an additional amount of glycerol (0.165 cc) was added and the mixture held at 1° to 8° C. for an additional 15 minute period, following which a third addition of glycerol was added to the mixture. Samples were selected for insemination from the sperm population at the bottom of the tube representing less than 4½% of the total population. Collected samples of sperm were then deep frozen using standard procedures as normally practiced in the artificial insemination industry.

As needed, sperm samples prepared as above, were removed from cold storage and used in artificial insemination of female mammals. In the specific case of cattle, cows found to be in heat were inseminated with 1 to 2 ccs containing at least 10 to 20 million sperm (before freezing), again using procedures standard in the artificial insemination industry. Sperm purity as determined by laboratory testing was in excess of 70% with the procedure described.

In the specific procedure being described, 13 of the cows inseminated became pregnant, and their fetuses killed and examined after a period of approximately 60 days. The results of these 13 pregnancies are set forth it Table 2 below:

TABLE 2

| Date Insem. | Run No. | Female No. | Govt. Lab. | Result |
|---|---|---|---|---|
| 5-15-67 | 53 | H-77 | 1328 | F |
| 6-6-67 | 70 | H-73 | 1328 | F |
| 1-27-68 | 212 | H-62 | 900 | F |
| 6-6-68 | 314 | CH-67 | 1812 | F |
| 7-23-68 | 361 | CH-365 | 1968 | F |
| 7-24-68 | 358 | CH-430 | 1812 | F |
| 7-24-68 | 362 | CH-386 | 1812 | F |
| 7-27-68 | 365 | CH-364 | 1968 | M × 2[1] |
|  |  | CH-55 | 1968 |  |
| 8-1-68 | 368 | CH-431 | 1968 | F × 2[2] |
| 8-4-68 | 370 | CH-349 | 1968 | F |
| 8-6-68 | 371 | CH-42 | 1968 | M |
| 8-7-68 | 372 | CH-366 | 1968 | F |
| 8-8-68 | 373 | CH-352 | 1968 | M |

[1]This run (No. 365) was inseminated into two cows. Each produced a male calf.
[2]This run (No. 368) produced twin female calves.

In analyzing the results of Table 2, run No. 365 was treated as if one male calf had been produced, and run No. 368 was treated as if a single female calf had been produced. It is to be noted that 13 females were expected, and that 10 females were actually obtained as against 3 males. This represents statistically significant departure from the normal sex ratio in cows.

I claim:

1. A method for separating X sperm and Y sperm according to phenotypic differences to make possible the control of the sex of mammalian offspring, comprising the steps of mixing fresh sperm with a nutrient medium; cooling the mixture of sperm and medium to a low temperature to immobilze the sperm; introducing the cooled mixture of sperm and medium to a separation medium in the form of a separate body of nutrient medium, at least part of said separation medium being substantially equivalent in density to the density of said mixture and having a uniform density gradient extending from a lightest density at the top to a heaviest density at the bottom; applying buoyant forces to the sperm introduced to said separation medium tending to separate the sperm at levels of suspension within the separation medium according to individual sperm density; and separating a portion of the separation medium of known density containing a suspended sperm fraction of equivalent density and desired predetermined sex characteristics.

2. A method as in claim 1 wherein the fresh sperm is introduced to the separation medium at an intermediate point as respects the density gradient so that less dense sperm rise to upper portions of the separation medium while more dense sperm sediment into the lower portions of the separation medium.

3. A method as in claim 1 wherein a bottom portion of the separation medium is separated thereby to isolate a bottom sperm fraction comprising substantially pure X-sperm.

4. A method as in claim 1 wherein a top portion of the separation medium is separated thereby to isolate a top sperm fraction comprising substantially pure Y-sperm.

5. A method as in claim 3 wherein the separated portion of the separation medium contains less than 10 percent of the total sperm population.

6. A method as in claim 4 wherein the separated portion of the separation contains less than 10 percent of the total sperm population.

7. A method as in claim 1 wherein said separation media contains at least one member of the group consisting of whole mammalian milk, cream, nonfat milk, egg yolk, dextrose, coconut cream, tomato juice, glucose, fructose, sugar alcohols, lecithin, amino acids, living body fluids and tissue extracts.

8. A method as in claim 1 wherein all portions of said separation media have a density between about 1.010 and 1.150 grams per cc when measured at 0° C.

9. A method as in claim 1 wherein said separation media has an osmolility within the range from about 276 to 280 milliosmos.

10. A method as in claim 1 wherein said separation media has a viscosity between about 2.00 to about 9.0 centipoise when measured at 0° C.

11. A method as in claim 1 wherein said sperm is a member of the group consisting of primates, cattles, pigs, sheep, rabbit, buffalo, goat and horse sperm.

12. A method as in claim 1 wherein said sperm is cattle sperm.

13. A method as in claim 1 wherein said sperm is human sperm.

* * * * *